US00RE42488E

(19) United States
(12) Reissued Patent
Willeford

(10) Patent Number: US RE42,488 E
(45) Date of Reissued Patent: Jun. 28, 2011

(54) BRONCHOSCOPY OXYGENATION SYSTEM

(76) Inventor: Kenneth L. Willeford, Lancaster, PA (US)

(21) Appl. No.: 12/636,255

(22) Filed: Dec. 11, 2009

Related U.S. Patent Documents

Reissue of:
(64) Patent No.: 7,320,324
Issued: Jan. 22, 2008
Appl. No.: 10/825,356
Filed: Apr. 15, 2004

(51) Int. Cl.
*A61M 11/00* (2006.01)
(52) U.S. Cl. ..... 128/207.16; 128/200.26; 128/205.24
(58) Field of Classification Search ..... 128/207.16, 128/200.26, 205.24, 912
See application file for complete search history.

(56) References Cited

U.S. PATENT DOCUMENTS 2,162,242 A 6/1939 Branower
3,774,604 A 11/1973 Danielsson
5,003,963 A * 4/1991 Bullard et al. ..... 600/104
5,183,031 A * 2/1993 Rossoff ..... 600/131
5,329,921 A 7/1994 Socaris et al.
5,354,267 A 10/1994 Niermann et al.
5,735,271 A 4/1998 Lorenzen et al.
5,746,199 A 5/1998 Bayron et al.
5,766,211 A 6/1998 Wood et al.
6,425,535 B1 7/2002 Akiba
6,652,453 B2 * 11/2003 Smith et al. ..... 600/188
2004/0206354 A1 * 10/2004 Fisher et al. ..... 128/204.23

* cited by examiner

*Primary Examiner* — Steven O Douglas
(74) *Attorney, Agent, or Firm* — Connolly Bove Lodge & Hutz LLP

(57) ABSTRACT

A bronchoscopy oxygenation system having a channel for inserting alternately an instrument or fluids and for delivering oxygen to a patient. The system being provided with pressure relief vent and a pressure relief valve for the relief of excessive oxygen pressure. The bronchoscopy oxygenation system may be used during bronchoscopy and with patient suctioning, bronchoalveolar lavage or biopsy. The bronchoscopy oxygenation system is intended to be used with a conventional bronchoscope.

15 Claims, 4 Drawing Sheets

BRONCHOSCOPY OXYGENATION SYSTEM

Matter enclosed in heavy brackets [ ] appears in the original patent but forms no part of this reissue specification; matter printed in italics indicates the additions made by reissue.

FIELD OF THE INVENTION

The herein disclosed invention finds applicability in the field of pulmonary medicine: for example in patient diagnosis, aspirating, sampling and therapeutic delivery.

BACKGROUND OF THE INVENTION

Patients who have pulmonary (lung) symptoms may be candidates for bronchoscopies. There are two types of bronchoscopies; therapeutic and diagnostic. Therapeutic bronchoscopy is to provide a treatment or therapy, and diagnostic is to aid in the diagnosis of an underlying condition. The bronchoscope is attached to a light source and advanced through the nares or mouth of the patient. Some bronchoscopes allow the pulmonologist to view the placement of the tip of the bronchoscope on a monitor from a video chip, and other models have an eye piece for viewing. Local anesthetics are often administered through the bronchoscope as it is advanced through the posterior pharynx and into the lungs. With direct visualization and manipulation of the tip with directional control, the vocal cords are identified and the instrument advanced into the trachea. Because of protective airway reflexes and the unpleasant nature of the procedure, the patient is likely to have received sedative medications that will decrease the respiratory drive. The respiratory rate will be decreased and the depth will be shallow. Consequently, oxygen delivery to the patient is reduced.

Once the bronchoscope is within the pulmonary system, it is intermittently advanced and withdrawn with directional control to access desired portions of the patient's lung. Diagnostic modalities afforded by this procedure include visualization of the trachea, bronchi, and bronchioloes for identification of abnormal tissue or secretions, as well as the ability to obtain biopsy specimens for laboratory analysis of tissue identification. Biopsy specimens are obtained by passing a biopsy forceps though the channel and excising a piece of tissue. Fluoroscopic x-ray guidance can be used intermittently throughout this procedure to aid in confirmation of the placement of the tip of the instrument.

The problem that is addressed with the new device of this invention is the problem of hypoxemia in patients who are having bronchoscopies. Hypoxemia is defined as reduced levels of oxygen in the blood and can be determined, measured, and quantified by pulse oximitry. Pulse oximitry is a standard monitor that measures the saturation of the oxygen carrying hemoglobin molecule.

In view of the problem of hypoxemia, there is a need in the medical field for a bronchial oxygenating system which is easy and safe to use; and when used along with a bronchoscope will provide oxygen through a channel of the bronchoscope when that channel is not in use.

Patent Literature

Lorenzen (U.S. Pat. No. 5,735,271) teaches a closed ventilation system apparatus which allows multiple access to the respiratory system through one or more access ports to ventilate the lungs with a gas or gases; to aspirate, oxygenate and visually inspect the respiratory system and/or take tissue samples. The herein disclosed system is unique in being an open, rather than a closed ventilation system. In addition Lorenzen does not show a pressure sensitive relief valve or a method of reducing standard hospital pressure through a controlled venting prior to patient application.

Bayron (U.S. Pat. No. 5,746,199) teaches a device with an endotracheal tube having attached thereto having several entry ports.

Urrutia (U.S. Pat. No. 5,817,068) teaches a plurality of feeds to a main conduit. Urrutia is directed to the use of fluids rather than oxygen.

Wood (U.S. Pat. No. 5,766,211) is for a device with a canal with a three-way valve for feed into the canal. Wood is directed to the use of fluids rather than oxygen, and does not show a pressure relief valve or a method of reducing standard hospital pressure through a controlled venting prior to patient application.

Akiba (U.S. Pat. No. 6,425,535) is for a fluid supplying apparatus for a cleaning the observation window of an endoscope.

Socaria (U.S. Pat. No. 5,329,921) discloses an endotracheal device allowing for the performance of various medical procedures while maintaining continuity of respiration.

OBJECTS OF THE INVENTION

A main object of the invention is to produce a bronchoscopy oxygenation system that is simple and easy to use.

A further object of the invention is to produce a device which is easy for the pulmonologist who may also be providing conscious sedation to use.

An important object of this invention is to produce a device which is able to safely supply oxygen to the patient and is safe for the doctor to use.

Another important object of the invention is to produce a device which can be conveniently used along with a conventional bronchoscope.

These and other objects of the present invention will become apparent from a reading of the following specification taken in conjunction with the enclosed drawings.

SUMMARY OF THE INVENTION

The herein disclosed invention is directed to a new bronchoscopy oxygenation system, the goal of which is to deliver oxygen directly to the lungs of patients during therapeutic and diagnostic bronchoscopy in order to reduce hypoxia or hypoxemia during the procedure. Hypoxia is derived from three main causes: First, during bronchoscopy, patients are given sedative medications which decrease their respiratory effort, so less oxygen is delivered to the lung. Second, the size of the bronchoscope which may be large compared to the size of the opening between the vocal cords can create a mechanical obstruction impeding oxygen delivery. The third and most significant cause of hypoxia is the elimination of air and oxygen from the lungs during suctioning performed to remove secretions and improve visualization as well as suctioning for bronchoalveolar lavage. These factors combine to place these patients at risk for complications related to depressed levels of oxygen in their blood.

The bronchoscopy oxygenation system of this invention is particularly useful in those surgical situations in which the patient is susceptible of receiving reduced oxygen during the procedure. Surgical procedures in which the system can be used are for example:

Bronchoalveolar lavage which is a technique that can be both diagnostic and therapeutic in nature. In this process, fluid is administered through the channel into the lung airways and then recovered and collected with the use of suction which is attached to the channel of the bronchoscope. This process can be of diagnostic value as the fluid will contain cells from the patient's lung which can be analyzed in the laboratory for tissue identification. In addition, bronchoalveolar lavage can be a therapeutic technique by removing excess and harmful secretions that are found in the bronchoalveolar system. Improved flow and respiratory gas exchange can result following this technique.

Obtaining of tissue specimens. Biopsy specimens are obtained by passing a biopsy forceps through the channel and excising a piece of tissue. Fluoroscopic x-ray guidance can be used intermittently throughout this procedure to aid in confirmation of the placement of the tip of the instrument.

Suctioning to remove fluids for laboratory analysis or to remove secretions that interfere with visualization. Suctioning is performed to obtain fluid and secretions as determined by the needs of diagnostic modalities or treatment options. In addition, suctioning is intermittently and frequently performed throughout the procedure to facilitate visualization by the pulmonologist, as excess secretions within the lung can obscure visualization during the procedure. This suctioning actively removes oxygen from within the lung, further leading to reduced oxygen delivery to the respiratory gas exchange membranes and resulting in hypoxemia.

In using the bronchoscopy oxygenation system of the invention along with a bronchoscope, the functions of the bronchoscope are not impeded. The primary intent of the design of the bronchoscopy oxygenation system of this invention is to utilize the single channel of a bronchoscope to provide oxygen at times when the primary channel is not otherwise in use. This channel can be accessed through the biopsy valve and currently has three functions. It can be used to obtain tissue biopsies by passing a biopsy forceps down the channel. The channel can be used to administer fluids such as saline into the lungs to combine with the fluid and secretions in the lung for bronchoalveolar lavage. The channel can be used for suctioning to remove fluids for laboratory analysis or to remove secretions that interfere with visualization. The invention proposes using this channel for the purpose of administering oxygen. Most of the time during bronchoscopy, this channel is not used for biopsies, lavage or suctioning. This provides an opportunity to pass oxygen through the bronchoscope to be delivered directly into the lungs at the distal tip of the instrument. The bronchoscopy oxygenation system of the invention is an open system rather than a closed system. A closed system is one in which there is a seal preventing communication between the system and the atmosphere. The closed system is generally used when patient can no longer breathe on his own. In the open system, no sealing is present between the patient's respiratory system and the oxygen supply means.

The simplicity of the brochoscopy oxygenation system of the invention is advantageous in all settings. The new design bronchoscopy oxygenation system utilizes a means that will allow for the safe administration of oxygen and still allow biopsies, lavage or suctioning. The system allows for a shared function of the channel in a bronchoscope. Oxygen can be administered from a standard oxygen flow meter and delivered to patient from the distal tip of the device. The oxygen flow can be interrupted when necessary for bronchoalveolar lavage or to obtain a biopsy specimen, but could continue during suctioning. The oxygen flow can be interrupted by turning the stopcock, which allows access to the biopsy valve for the other purposes. Interruption of oxygen flow creates a safety hazzard, as the oxygen supply tubing will be holding pressure equal to the oxygen outlet pressure of 50 psi. When this pressure is allowed to access a syringe, the plunger becomes a forceful projectile that is of concern for personnel. If the pressure is allowed to pass through the bronchoscope, it may cause patient harm from barotrauma. This safety issue has been resolved by the use of a pressure relief vent designed to reduce standard hospital pressure (50 psi) to a level that would be safe for patient application, and an additional backup safety pressure relief valve built into the device. The pressure relief valve is set at 40 cm of water which will provide safety to the patient from any surge in pressure. The invention could consist essentially of the system as herein defined.

DESCRIPTION

Figure 1:
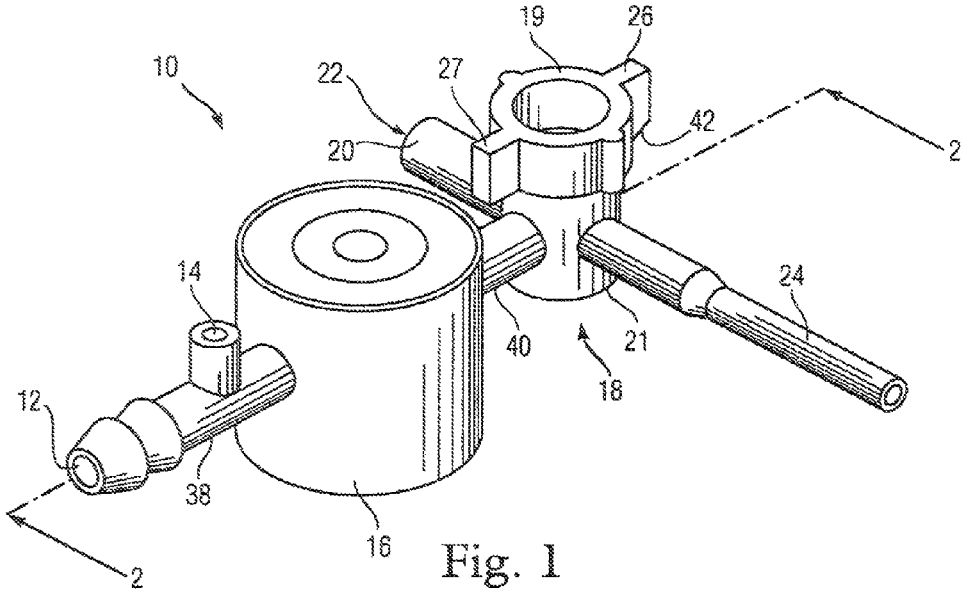
FIG. 1 is a perspective view of the Bronchoscopy Oxygenation System of this invention.

Referring to FIG. 1, the bronchoscopy oxygenation system of the herein disclosed invention 10 has an oxygen entry orifice 12 and a pressure relief vent 14, feeding to a pressure relief valve 16 which, in turn, is attached to a stopcock housing 18, the top 19 swivels and the bottom 21 is fixed. Through the stopcock housing 18 runs an instrument insertion channel 20 having a proximal end 22 and a distill tip 24. Attached to the stopcock housing 18 is top 19 having stop handle 26 and plain handle 27. Stop handle 26 has a stop tab plate 42 attached thereto and is intended to engage arrest tubs 44 and 45 (FIG. 3C) for the purpose of properly aligning channels of the stopcock, as will be explained. Handle 27 has no stop tab and functions simply as a handle.

There are two possible positions of the stopcock. FIGS. 3A-3D illustrate the instrument access position. In the access position the stopcock is turned so the stop tab plate 42 of stop handle 26 is against arrest tab 44. FIGS. 4A-4D illustrate the standard or oxygen access position. In the standard position the stop tab 42 of stop handle 26 is against arrest tab 45. These two stopcock positions can most easily be seen by comparing FIG. 3C with FIG. 4C.

Figure 3A:
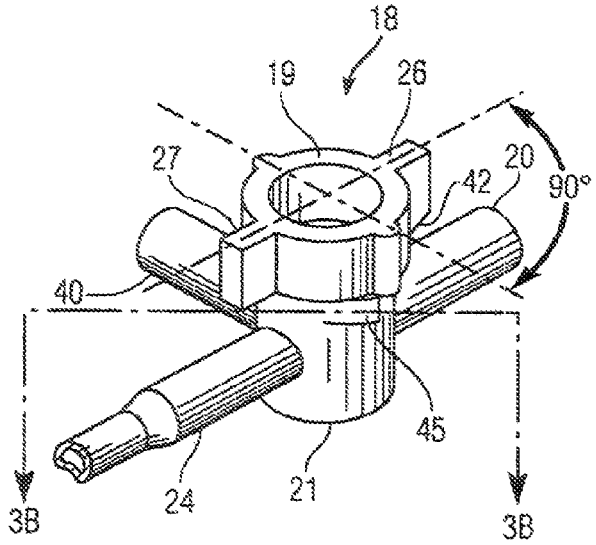
FIG. 3A is a perspective view of the stopcock.
Figure 3B:
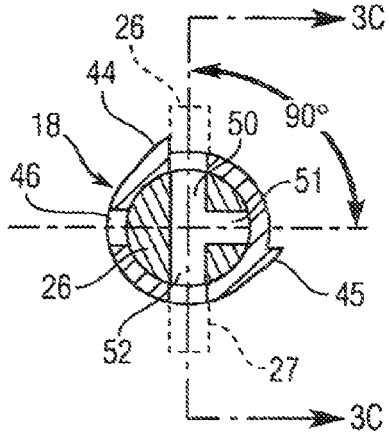
FIG. 3B is a cross-section taken along lines 3B-3B of FIG. 3A.
Figure 3C:
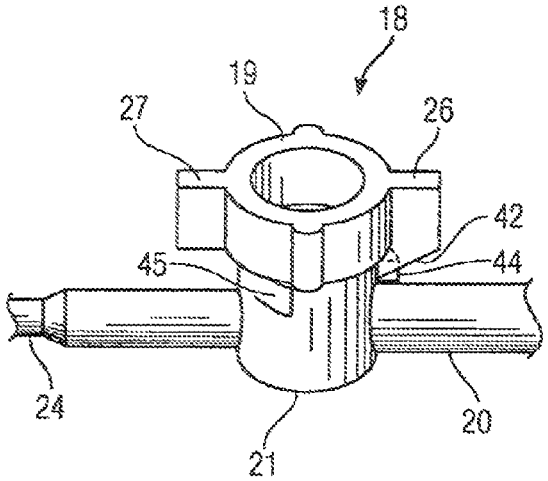
FIG. 3C is a perspective of the stopcock taken at a slightly different angle from FIG. 3A.

The instrument access position (FIGS. 3A-3D) functions to allow the stopcock channels to align with the instrument insertion channel 20 and distal end 24 to allow for the passage of an instrument or fluids. In FIGS. 3A and 3B, the crossed dashed lines show the position of the handles and the arrows show the direction and degree of turn of the handles.

Figure 4A:
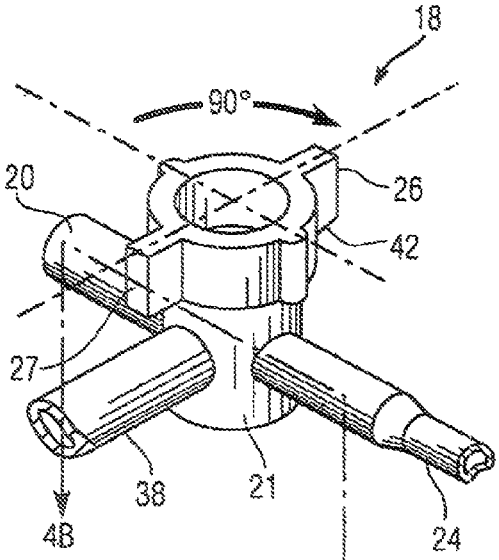
FIG. 4A is a perspective view of the stopcock.
Figure 4B:
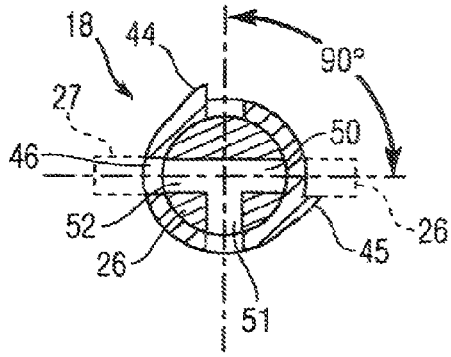
FIG. 4B is a cross-sectional view of the stopcock taken along lines 4B-4B.
Figure 4C:
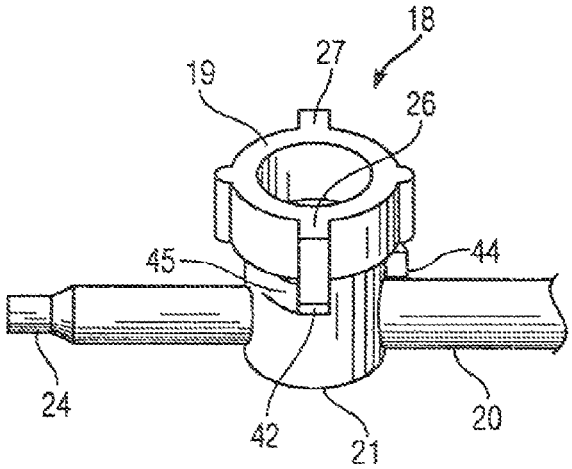
FIG. 4C is a perspective view of the stopcock similar to FIG. 4A.

The standard position (oxygen) (FIGS. 4A-4D) is created by turning the stopcock handles 26 and 27 90° which lines up the channels to allow for the passage of oxygen. In FIGS. 4A and 4B, the crossed dashed lines across the stopcock show the position of the handles and the arrow in FIGS. 4A and 4B show the direction in which the handles are turned as well as the degree of turn. In the standard position oxygen is supplied through the path entry orifice 12, tube 38, reservoir housing 16, tube 40, leading to stopcock entry 46 and then paths 52 and 51 (FIGS. 1, 4B, 4D) and then to distal end 24.

Figure 2:
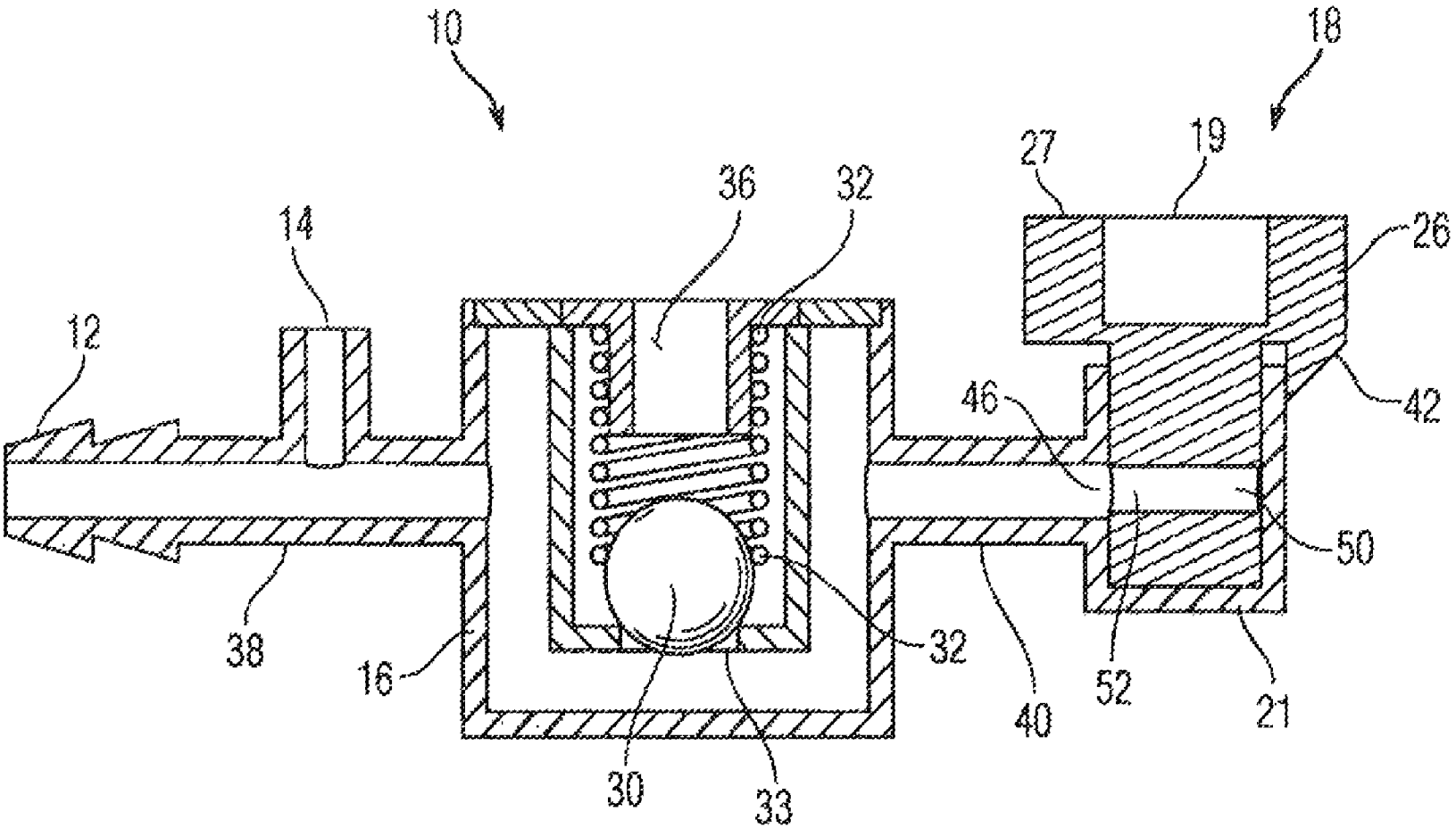
FIG. 2 is a cross-section view thereof taken along lines 2-2 of FIG. 1.
Figure 4D:
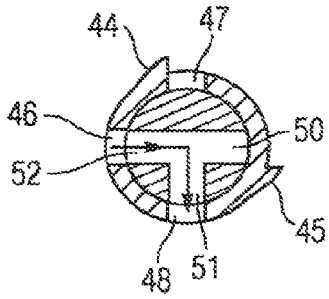
FIG. 4D is a cross-sectional view of the channel arrangement of the stopcock position of FIG. 4A.

Referring to FIG. 2, contained in the reservoir housing 16 is a pressure retaining ball 30 and a pre-loaded spring 32 forming a backup safety pressure relief valve. When the backup safety pressure relief valve is activated by an excess of pressure of oxygen, the excess pressure will cause pressure retaining ball 30 held in place by pre-loaded spring 32 to lift from valve seat 33 and allow oxygen to vent to the outside through vent opening 36. Also, shown in FIG. 2 is the stopcock 18 having bundle 27, stop plate handle 26 with stop tab 42 and arrest bumper 44 (not shown) all in top 19 of the stopcock 18. The position of the stopcock 18 allows passage of oxygen from tube 40 to stopcock entry 46 and to channel members 52 and 51 (FIG. 4D).

With reference to FIG. 1, in operation, oxygen at 50 psi (standard in operating rooms) enters the devise 10 through standard neoprene tubing (not shown) at entry orifice 12. The pressure relief vent 14 is sized to bleed off pressure to 40 cm of water bin will allow airflow of approximately 3 liters per minute through the device. Oxygen then flows through the reservoir 16 and through the stopcock 18 and channels 52 and 51 flowing out of the tip 24 which is inserted into the biopsy port of a bronchoscope (not shown). In the reservoir housing 16 there is a backup safety pressure relief valve, which consists of a pressure retaining a ball 30 and a pre-loaded spring 32 which when activated will open and vent through opening 36. The activation event of a surge of oxygen pressure greater than 40 cm of water will cause the pressure retaining ball 30 to leave valve seat 33 to vent.

The pressure relief vent 14 and pressure relief valve will function in both the access and standard positions to prevent excessive oxygen pressure build-up within the system.

With reference to FIGS. 3A-3D and 4A-4D the two stopcock positions are shown which place the device in the access (instrument) or standard (oxygen) positions respectively.

With reference to FIGS. 3B and 4B, a cross section of the stopcock is shown. Particularly note the positions of arrest tabs 44 and 45 which are to bump against stop plate 42 to align the stopcock for the access and standard positions respectively (best shown in FIGS. 3C and 4C).

Figure 3D:
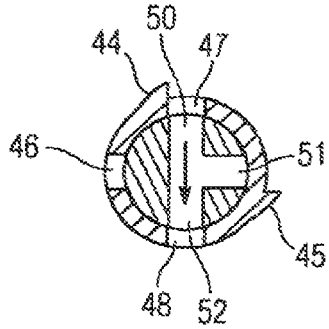
FIG. 3D is a view of the channel arrangement of the stopcock position of FIG. 3A.

With reference to FIG. 3D, there is schematically shown the access position for the stopcock. This illustrates the position of the stopcock to allow the passage of an instrument or fluids while in the access position through entry 47 along path 50 and 52 to exit 48 to tube 24. There is no oxygen flow through the stopcock in the access position. The arrow indicates the direction an instrument or fluids would take while in the access position.

In FIG. 4D the arrow shows the path of oxygen through the stopcock while in the standard position. The oxygen path is through entry 46 along channel paths 52 and 51 to exit 48 and tube 24.

Figure 5A:
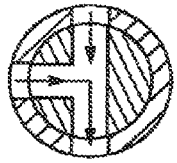
FIG. 5A is a cross-sectional view of a channel arrangement of the stopcock position that is not utilized in this design.

There is another theoretical position of the stopcock shown in FIG. 5A. This would allow the passage of both an instrument and oxygen. This possible position was excluded form this design for practical clinical considerations. The arrows show the path that an instrument and oxygen would take.

Detailed Description of Use

The procedure for using the bronchoscopy oxygenation system will be to insert the device into the biopsy port of a bronchoscope. The oxygen tubing will be connected from an oxygen flow meter to the device. The flow meter will be adjusted to approximately 10 liters of oxygen per minute. The stopcock position will initially be in the standard position (oxygen) (FIG. 4A-4D). When bronchoalveolar lavage is performed or tissue biopsies are obtained, the stopcock will be placed in the access position (FIG. 3A-3D). Once the lavage or biopsies are completed, the stopcock will be returned to the standard position (FIG. 4A). The stopcock can be rotated 90 degrees to configure the device in either the access or standard position. In the access position a standard 2 mm biopsy instrument can be inserted or bronchoalveolar lavage performed without the need to remove the device from a bronchoscope The bronchoscopy oxygenation system can be employed with the stopcock in the standard or access positions as described. The standard position would be in use in the majority of times. This position allows for delivery of oxygen through the bronchoscope and would have the third access port of the stopcock closed. This position can also be utilized during suctioning.

In the suctioning mode, the suction is connected to a bronchoscope in a continuous fashion. This port has an internal connection to the single channel of the bronchoscope and is made to be continuous when the pulmonologist depresses a button on the bronchoscope. When this button is not depressed, the reduced barometric pressure of the suction is isolated from the single channel. This configuration allows the suction to be used with the bronchoscopy oxygenation system of this invention in either the standard or access positions.

The access position is employed while obtaining tissue biopsies, during bronchoalveolar lavage, or when other fluids such as local anesthetics are administered. In this position there is no oxygen flow through the channel. In practical use, the percentage of total procedural time in this position is minimal.

In both the standard and access positions the pressure relief vent and the backup safety pressure relief valve will ensure a safe environment for both the patient and medical team.

Advantages to using the system of the invention are:

The system can be used during many pulmonary medicine procedures involving the lungs or bronchi where there is reduced oxygen at the respiratory gas exchange membranes in patients having bronchoscopies. The bronchoscopy oxygenation system of this invention will solve this problem by administering oxygen through the channel directly into the lungs. This oxygen delivery will be independent of reduced patient respiratory drive from intravenous medications, and also independent of the mechanical obstruction at the vocal cords created by the bronchoscope.

The bronchoscopy oxygenation system has taken into consideration safety and has built-in safety features. Barotrauma to the lungs is a potentially serious consideration. The system has to be able to deliver an adequate flow of oxygen through a bronchoscope so as to aid in oxygenation of the patient, while limiting the pressure of delivered gasses to avoid barotrauma. This required knowledge of oxygen utilization and pulmonary physiology. These considerations were inherent in the final design and a redundant system for pressure relief was engineered. An additional consideration was the safety of personnel. The wall source of oxygen is delivered at a pressure of 50 pounds per square inch. This source needed to be adapted so oxygen could be delivered to the patient in a manner that was safe for both the patient and health care personnel.

Obviously, many modifications may be made without departing from the basic spirit of the present invention.

Accordingly, it will be appreciated by those skilled in the art that within the scope of the appended claims, the invention may be practiced other than has been specifically described herein.

What is claimed is:

1. An open bronchoscopy oxygenation system comprising, a) an orifice for receiving oxygen joined with, b) a reservoir housing containing a pressure relief valve, to prevent excessive oxygen pressure, c) a stopcock attached to an oxygen passage for receiving oxygen and further attached to an instrument passage for receiving an instrument, and with the stopcock being supplied a handle controlling the flow through the oxygen passage and instrument passage, thus allowing for the passage of oxygen and/or an instrument through said oxygen passage and/or instrument passage, and d) with the position of the stopcock allowing for the passage of either oxygen, an instrument or fluids to a patient such that the patient may be safely treated.

2. The open bronchoscopy oxygenation system of claim 1 wherein there is a pressure relief vent provided between the orifice for receiving oxygen and said pressure relief valve.

3. The open bronchoscopy oxygenation system of claim 1 wherein the stopcock is supplied with a handle and a stop-tab arrangement wherein the stopcock can be turned in a direction allowing for passage of oxygen or the passage of an instrument.

4. A method of performing bronchoalveolar lavage in a patient employing an open bronchoscopy oxygenation system comprising, a) an orifice for receiving oxygen joined with, b) a reservoir housing containing a pressure relief valve, to prevent excessive oxygen pressure, c) a stopcock attached to an oxygen passage for receiving oxygen and further attached to an instrument passage for receiving an instrument, and with the stopcock being supplied with a handle controlling the flow through the internal passages, thus allowing for the passage of oxygen through the oxygen passage and/or the passage of an instrument through the instrument passage, and d) with the stopcock being attached to a passage running front said stopcock allowing for the passage of either oxygen, an instrument or fluids to a patient such that the patient may be treated, and e) with the method steps comprising the steps of supplying oxygen to the patient through said oxygen passage and turning the stopcock and performing bronchoalveolar lavage through said instrument passage.

5. The method of claim 4 wherein the open bronchoscopy oxygenation system is provided with a pressure relief vent between the orifice for receiving oxygen and said pressure relief valve.

6. A method of obtaining a tissue specimen from a patient comprising employing a bronchoscopy oxygenation system comprising, a) an orifice for receiving oxygen joined with, b) a reservoir housing containing a pressure relief valve, to prevent excessive oxygen pressure, c) a stopcock attached to an oxygen passage for receiving oxygen and further attached to an instrument passage for receiving an instrument, and with the stopcock being supplied with a handle controlling the flow through the oxygen passage and instrument passage, thus allowing for the passage of oxygen and/or an instrument through said oxynen passage and/or instrument passage, and d) with the position of the stopcock allowing for the passage of either oxygen, an instrument or fluids to a patient such that the patient may be safely treated, and e) with the method steps comprising the steps of alternately supplying oxygen to the patient through said oxygen passage and turning the stopcock to perform a biopsy through said instrument passage with a biopsy forcep and in that way preventing hypoxemia in said patient while said tissue specimen is obtained.

7. the method of claim 6 wherein the open bronchoscopy oxygenation system is provided with a pressure relief vent between the orifice for receiving oxygen and said pressure relief valve.

8. A method of suctioning of a patient comprising employing an open bronchoscopy oxygenation system comprising, a) an orifice for receiving oxygen joined with, b) a reservoir housing containing a pressure relief valve, to prevent excessive oxygen pressure, c) a stopcock attached to an oxygen passage for receiving oxygen and further attached to an instrument passage for receiving an instrument, and with the stopcock being supplied with a handle controlling the flow through the oxygen passage and instrument passage, thus allowing for the passage of oxygen and/or an instrument through said oxygen passage and/or instrument passage, and d) with the position of the stopcock allowing for the passage of either oxygen, an instrument or fluids to a patient such that the patient may be safely treated, and e) with the method steps comprising the steps of altemately supplying oxygen to the patient through said oxygen passage and turning the stopcock and performing suctioning through said instrument passage and in that way preventing hypoxemia in said patient while performing suctioning.

9. The method of claim 8 wherein the open bronchoscopy oxygenation system is provided with a pressure relief vent between the orifice for receiving oxygen and said pressure relief valve.

*10. An open bronchoscopy system comprising:*

*a) an orifice for receiving a gaseous substance;*

*b) a pressure relief vent coupled between the orifice and a passage for the gaseous substance;*

*c) a stopcock coupled to the passage, and further coupled to an instrument passage to receive an instrument, wherein the stopcock is configured with a handle to control a flow through the passage and instrument passage, wherein the stopcock is configured such that the position of the stopcock is to permit the passage of either the gaseous substance or a non-gaseous substance to a patient.*

*11. The bronchoscopy system of claim 10, wherein said non-gaseous substance comprises an instrument or a fluid.*

*12. The bronchoscopy system of claim 10, wherein said gaseous substance comprises oxygen.*

*13. The bronchoscopy system of claim 10, wherein the stopcock includes a handle and a stop-tab arrangement to permit the stopcock to be turned in a direction allowing for passage of the gaseous substance or a direction allowing for the passage of a non-gaseous substance.*

*14. The bronchoscopy system of claim 10, further comprising a reservoir coupled to the pressure relief vent and arranged to receive the gaseous substance.*

*15. The bronchoscopy system of claim 14, wherein the reservoir comprises a pressure relief valve.*

* * * * *